United States Patent [19]

Baldwin

[11] Patent Number: 4,708,862
[45] Date of Patent: Nov. 24, 1987

[54] RADIOIMMUNO DETECTION OF HUMAN CANCERS USING ANTI-TUMOR MONOCLONAL ANTIBODY

[75] Inventor: Robert W. Baldwin, Long Eaton, United Kingdom

[73] Assignee: Xoma Corporation, Berkeley, Calif.

[21] Appl. No.: 875,256

[22] Filed: Jun. 17, 1986

Related U.S. Application Data

[63] Continuation of Ser. No. 468,193, Feb. 22, 1983, abandoned.

[51] Int. Cl.⁴ ............... A61K 43/00; A61K 39/00; C12N 5/00; G01N 33/577
[52] U.S. Cl. ............... 424/1.1; 424/9; 424/85; 436/548; 435/68; 435/240.27; 435/172.2; 530/387; 530/389; 530/808; 530/809; 935/103; 935/104; 935/107; 935/108; 935/110
[58] Field of Search ............... 424/1.1, 9, 85; 436/548; 530/387, 389, 808, 809; 935/103, 104, 107, 108, 110; 435/68, 240, 172.2

[56] References Cited

U.S. PATENT DOCUMENTS

| 4,349,528 | 9/1982 | Koprowski et al. | 424/85 |
| 4,444,744 | 4/1984 | Goldenberg | 424/1.1 |
| 4,471,057 | 9/1984 | Koprowski et al. | 436/518 |
| 4,472,371 | 9/1984 | Burchiel et al. | 424/1.1 |

OTHER PUBLICATIONS

Herlyn et al., Proc. Natl. Acad. Sci., U.S.A., 76 (1979) 1438-42.
Koprowski et al., Proc. Natl. Acad. Sci. U.S.A., 75 (1928) 3405-9.
Farrands et al., The Cancer, Aug. 21, 1982, pp. 397-400.
Herlyn et al., Cancer Research 40 (1980) 717-21.
Embleton et al., Chemical Abstracts, 98 (1983) #172695v.
Embleton et al., Chemical Abstracts, 95 (1981) #95310z.

*Primary Examiner*—Christine M. Nucker
*Attorney, Agent, or Firm*—Townsend and Townsend

[57] ABSTRACT

The present invention relates to the radioimmuno detection of cancers by detecting tumor associated antigens and comprising the following steps:

(i) preparing samples of hybridoma XMMCO-791 as herein described,
(ii) separating and purifying the associated antibody produced by XMMCO-791 hybridomas to obtain the IgG2b isotype,
(iii) labelling the antibody thus obtained with a radio active label,
(iv) preparing composition containing an effective concentration of said labelled antibody
(v) administering said antibody composition to a patient and
(vi) thereafter screening said patient to detect concentrations of radioactivity thereby indicating a concentration of antibody.

Hybridoma cell line XMMCO-791 was deposited with the American Type Culture Collection (A.T.C.C.), Rockville, MD 20852-1776, on Aug. 14, 1986, and given A.T.C.C. Accession No. HB 9173.

7 Claims, 5 Drawing Figures

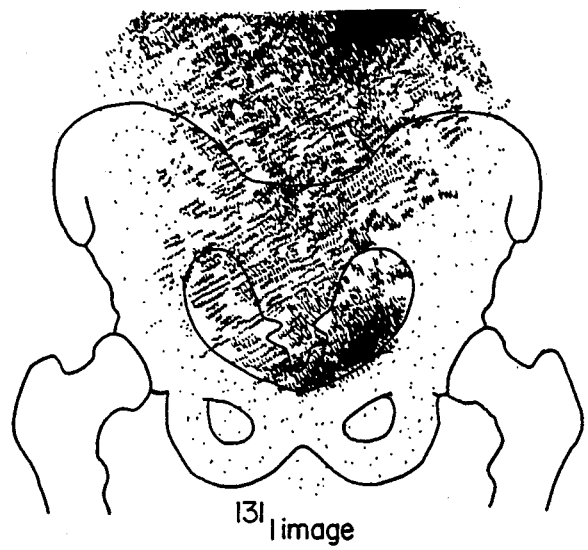
FIG._1A.
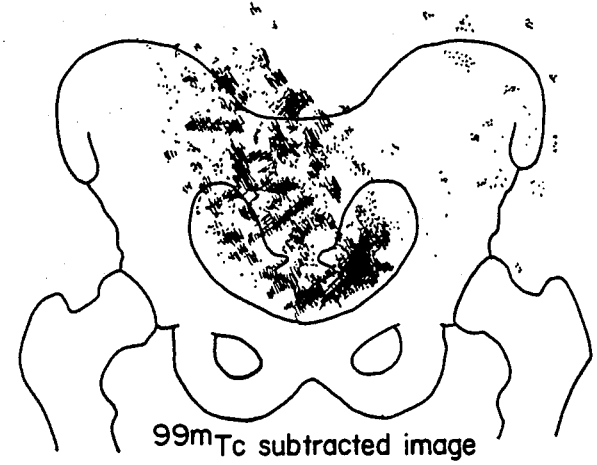
FIG._1B.

113mIn subtraction
FIG._2.
FIG._3A.
100cm
FIG._3B.

RADIOIMMUNO DETECTION OF HUMAN CANCERS USING ANTI-TUMOR MONOCLONAL ANTIBODY

This is a continuation of Ser. No. 468,193, filed Feb. 22, 1983, now abandoned.

DESCRIPTION

The present invention relates to the radioimmuno detection of human cancers by antitumour monoclonal antibodies. It is well known that radioactively labelled antibodies directed against tumour associated antigens can detect cancer deposits within the body. The present invention relates to a specific monoclonal antibody which reacts with human malignant colorectal cells which antibody has been labelled with radio active material.

The method of the invention has been found to provide a fascile means of diagnosing with precision the presence and position of a cancer deposit particularly in the colorectal region.

According to the present invention there is provided a method of detecting tumour associated antigens which method comprises:

1. preparing samples of hybridoma XMMCO-791 clone 3 as herein described.
2. separating and purifying the associated antibody produced by XMMCO-791 hybridomas to obtain the IgG2b iostype.
3. labelling the antibody thus obtained with the radio active label.
4. preparing a composition containing an effective concentration of said labelled antibody.
5. administering said antibody composition to a patient,
6. thereafter screening said patient to detect concentrations of radioactivity thereby indicating a concentration of antibody and presence of a cancer deposit.

The antibodies are preferably labelled with iodine 131. The screening may be carried out using a gamma camera. The image obtained using a gamma camera may be enhanced using an image enhancement technique which may further include blood cell and blood transferring labelling using isotopes selected from at least one of the group consisting of 99 m Tc and 113 m In.

Following is a description by way of example only with reference to the accompanying drawings of methods of carrying the invention into effect.

In the drawings:

FIG. 1 is an anterior radionuclide image of the pelvis showing the localisation of antibody before image enhancement.

FIG. 1b is an anterior radionuclide image of the pelvis showing localisation of the antibody after enhancement.

FIG. 2 illustrates the presence of a secondary in the brain of one of the patients.

FIG. 3a is a radionuclide image of resected specimen; and

FIG. 3b is a microscopic section of bowel showing a nodular tumour with a small associated polyp in the adjacent colon wall.

EXAMPLE 1

Development of the hybridoma

Male Balb/c mice are injected interperitoneally with $10^7$ cells of osteogenic sarcoma cell line 791T. One week later a second interperitoneal inoculation of $10^7$ 791T cells is given and the mice are then given a booster inoculation of $2 \times 10^6$ 791T cells by intracardiac injection five days before their spleens are removed for fusion.

The spleens are removed aspectically and cell suspensions are prepared by teasing fragments in RPM1 1640 medium. $10^8$ spleen cells are then fused with $10^7$ P3NS1 cells using 50% polytheylene glycol. The supernatants are then screened for reactivity against 791T cells and other targets using a 125I labelled Protein A binding test. Positive hybridomas are then cloned in 0.3% agar as described by Gunn et al Int. J. Cancer 26; 1980; 325–330. Essentially, antibody-positive mass cultured hybridoma cells were suspended in 0.3% agar in RPMI + 10% FCS and seeded over a thin layer of 0.5% agar overlying a feeder layer of rat peritoneal exudate cells in 25 cm$^2$ culture flasks. Colonies growing from single cells were isolated and grown separately. The supernatants of each clone were screened for anti-791T antibody and negative clones were discarded.

The antibodies were prepared by diluting the ascites fluid 1:1 in 0.1 molar citrate phosphate buffer at a pH of 7.5. The fluid so prepared is then passed through a Sepharose-Protein A column. After extensive washing of the column, immunoglobulins are eluted with citrate-phosphate buffer at a pH of 3 with a 12 ml/h flow rate using an LKB Ultragrad gradient mixer of the type supplied by LKB of South Croydon, Surrey, England. The material eluted at pH 3 is pooled, dialysed against phosphate buffer sulphate, and concentrated by positive pressure membrane ultra-filtration to produce monoclonal antibody designated XMMCO-791 monoclonal antibody. Hybridoma cell line XMMCO-791 was deposited with the American Type Culture Collection (A.T.C.C.), Rockville, MD 20852-1776, on Aug. 14, 1986, and given A.T.C.C. Accession No. HB 9173.

EXAMPLE 2

The antibody thus prepared is labelled with iodine 131 using the iodogen method described by Fraker and Speck in 1978.

For labelling purposes, 300 μl aliquots of iodogen (1,3,4,6-tetrachloro-3a,6a-diphenylglycouril as supplied the Pierce Chemical Co., Chester, Cheshire, England) are combined with 4 μg/ml of antibody in methylene chloride and are evaporated to dryness under nitrogen in conical polypropylene tubes, of the type supplied by Sarstedt of Leicester, Leicestershire, England. The sodium iodide isotype of iodine 131 of a grade suitable for protein iodination as supplied by the Radiochemical Centre, Amersham, Bucks., England, together with protein at a concentration of 1 mg/ml are added to the tubes and incubated for 15 min at room temperature. The reaction is stopped by removing the reaction mixture from the Iodogen-coated tubes. Free radioiodine is separated by the passage of rection mixture through Sephadex G25 in phosphate buffer sulphate (supplied by Pharmacia, of Uppsala, Sweden).

For this purpose, the antibody is labelled in 5 Mci $I^{131}$/500 μg of XMMCO-791 monoclonal antibody. The radioactivity in antibody preparations is counted and the antibody solution then sterilized by filtration through 0.22 micron membrane filters. 2 Mcl of sterilised preparation containing approximately 200 μg of antibody is then added to 200 ml of steril saline preparatory for administration by injection.

EXAMPLE 3

Eleven patients were studied, five were known to have primary rectal colon cancers, and six had extensive disseminated disease histologically confirmed at a previous laparotomy. One patient with a secondary disease had received a radiotherapy dose of 30 Gy to his inoperable rectal tumour 2 weeks before the infusion of radiolabelled antibody. Another patient had a discrete secondary in the brain and the remainder had disease restricted to the abdomen. The mean age of the patients was 64 years (44–75), 3 were female and 8 were male.

The nature of the study was clearly explained to the eleven patients who gave their informed consent. The thyroid uptake of radioiodine was blocked by 60 mg of potassium iodide per day for two weeks starting at least 24 hours before the injection of the antibody. One ml of antibody solution was injected subcutaneously into ech patient's right arm 30 minutes before the infusion of the antibody to test for anaphylaxis. Patients lymphocytes were tested in vitro with the antibody to ensure there was no cross-reaction with their normal cells.

Twenty-four hours after the administration of the $I^{131}$ labelled antibody, anterior and posterior images of the abdomen and pelvis were taken with gamma camera and recorded by computer. Other sites were imaged as required. Views were subsequently taken at 48 and 72 h in the patients not undergoing surgery.

Image enhancement was achieved by substraction of background radioactivity as described by DeLand et al in a paper entitled "Imaging approaching radioimmunodetection reported in Cancer Research 1980: 40: 3046-3409. The patients red blood cells were labelled in vivo with $^{99m}Tc$ and depending upon the position of the tumour, $^{113m}$In-labelled indium chloride solution was given to label the blood transferin. After normalisation to equalise the counts recorded in each image, the $^{99m}Tc$ and $^{131}$In-images of the blood pool were subtracted from the corresponding $^{131}$I-labelled antibody images. The tumours in the five patients with the primary cancers were resected 48 h after the administration of the $^{131}$I-labelled antibody and were then immediately imaged again to assess the distribution of the labelled antibody. The relative uptake of $^{131}$I-labelled antibody per gram of tissue was further determined by measuring the radioactive count rates from the tumours and by comparing these activities with count rates from adjacent areas of the normal colon tissue.

The results are set out in Table 1 as shown below:

| | | TUMOUR | |
|---|---|---|---|
| Patient | Age (Sex) | Macroscopic | Grade/ differentiation |
| 1 | 71 M | Primary nodular Ca of sigmoid (5 × 6 × 2 cm) | Moderate |
| 2 | 66 F | Primary nodular Ca rectosigmoid (4 × 4 × 3 cm) | Well |
| 3 | 75 M | Primary nodular Ca sigmoid (4 × 3 × 3 cm) | Moderate |
| 4 | 67 M | 2 primaries, transverse and rectum (3 × 3 × 2 cm, 4 × 3 × 4 cm) | Moderate |
| 5 | 64 M | Primary ulcerating Ca sigmoid (6 × 3 × 3 cm) | Well |
| 6 | 58 F | Disseminated Ca with omental 2° postop (10 × 15 × 3 cm) | Moderate |
| 7 | 71 M | Disseminated Ca with liver 2° postop (6 × 6 × 3 cm) | Moderate |
| 8 | 50 M | Disseminated Ca with 2° in liver postop | Moderate |
| 9 | 72 M | Inoperable Ca rectum treated by radiotherapy 30 GY | Moderate |
| 10 | 44 M | Disseminated Ca Caecum 2° in liver and brain postop (2 × 2 × 1 cm⁶ brain) | Moderate |
| 11 | 60 F | Disseminated Ca in sigmoid with pelvis recurrence (6 × 6 × 5 cm) | Moderate |

| | IMAGING | | | |
|---|---|---|---|---|
| | | | Tumour to non-tumour ratios | |
| Patient | Background Subtraction Agent | Site of image | Before Subtraction | After background subtraction |
| 1 | $^{99m}$TcRBC $^{113m}$In-transferrin | Positive; primary in pelvis | 1.5/1 | 8.0/1 |
| 2 | $^{99m}$TcRBC | Positive; primary in pelvis attached to bladder | 1.5/1 | 2.1/1 |
| 3 | $^{99m}$TcRBC | Not detected; behind bladder | . | . |
| 4 | $^{99m}$TcRBC | Positive for both epigastrium and pelvis | 1.5/1 | 2.1/1 |
| 5 | $^{99m}$TcRBC | Positive; primary in pelvis | 1.2/1 | 1.5/1 |
| 6 | $^{99m}$TcRBC | Positive; peritoneal and omental 2° | 2.0/1 | 8.1/1 |
| 7 | $^{99m}$TcRBC $^{113m}$In transferrin | Positive; pelvis and liver | 1.2/1 | 5.1/1 |
| 8 | $^{99m}$TcRBC | Positive; 2° in liver | 1.5/1 | 4.4/1 |
| 9 | $^{99m}$TcRBC; $^{99m}$Tc sulphur colloid $^{113}$In-transferrin | Not detected | — | — |
| 10 | $^{99m}$TcRBC $^{113m}$In-transferrin | Positive; 2° in brain and liver | 1.3/1 | 4.0/1 |
| 11 | $^{99m}$RBC; 113m In-transferrin | Positive; mass anterior to rectum | 1.9/1 | 4.3/1 |

Table 2 illustrates the results of postoperative imaging and counting of the five resected specimens.

| Patients | Tumour | Size of resected | Tumour to non-tumour ratio on image | Tumour to non-tumour counts gram of tissue |
|---|---|---|---|---|
| Case 1 | Primary nodular Ca sigmoid | 5 × 6 × 2 cm | 2.3/1 | 2.2/1 |

-continued

| Patients | Tumour | Size of resected | Tumour to non-tumour ratio on image | Tumour to non-tumour counts gram of tissue |
|---|---|---|---|---|
| Case 2 | Primary nodular Ca recto-sigmoid | 4 × 4 × 5 cm | 2.5/1 | 5.8/1 |
| Case 3 | Primary nodular Ca recto-sigmoid | 4 × 5 × 3 cm | Not imaged | 2.1/1 |
| Case 4 | 2 Primary ulcerating Ca rectum and transverse colon* | 3 × 3 × 2 cm<br>4 × 4 × 2 cm | 2.1/1<br>2.0/1 | 3.1/1<br>Not counted |
| Case 5 | Primary ulcerating Ca of sigmoid colon | 6 × 3 × 3 cm | 1.5/1 | 1.1/1 |

*Undiagnosed carcinoma identified on image.

From the foregoing it will be appreciated that all eleven patients tolerated the procedure well and there were no untoward reactions. Temperature and pulse rate remained stable during infusion and for two weeks after the injection, and during the pre-infusion incubation studies the patients' small lymphocytes did not cross react with the monoclonal antibody.

In 10 out of the 11 patients, the infused iodine-131-labelled antibody became localised within the cancer deposits shown in table 1 with a mean tumour to non-tumour ratio of 1.5/1 before subtraction and 4.4/1 after subtraction for the blood pool. In one of the negative preoperative studies, case 3, the subsequent images of the resected specimen were positive (Table 2) and failure initially to demonstrate this patient's tumour was thought to be the result of its being obscured by the bladder. The in vivo release of iodine 131 from the antibody and its excretion in the urine produced bladder images in all patients.

In the 9 cases with a positive image on the gamma camera, the imaged site exactly matched the site of the tumour documented clinically and at operation.

FIG. 1 (Case 6) shows a large omental mass arising from the pelvis of a woman with ascites and an obvious palpable recurrence. In case 4, not only was the primary rectal carcinoma identified preoperatively, but a hitherto undiagnosed second synchronous tumour was also seen; the barium enema examination had only demonstrated the original rectal cancer. In case 10, a seondary of the brain was clearly identified (see FIG. 2). This accorded with the patient's right hemiplegia and was later confirmed at necropsy. This was the smallest tumour identified. It measured 2×2×1 cm. There as no correlation between the stage, macroscopic appearance, or microscopic grade of any of the tumours and the uptake of antibody.

Four out of the 5 patients with primary tumours had a positive preoperative image (the negtive image was produced by the patient's bladder obscuring the tumour), and all resected specimens demonstrated uptake by the cancer deposits (see Table 2). The mean tumour to non-tumour uptake ratio in the specimens was 2.1 (range of 1.5 to 2.5/1); in case 4 two resected tumours were identified on imaging with uptake ratios of approximately 2/1. In every case the localisation of the iodine 131 labelled monoclonal antibody matched exactly the size and contours of the tumour. FIG. 3 demonstrates the degree of localisation achieved. Not only is the nodular tumour seen, but a 1 cm diameter polyp can also be clearly identified.

The count per gram of cancer tissue compared with that in the normal colon, in the resected specimens, ranged from 1.1/1 to 5.8/1 with a mean value of 2.8/1. In the two patients (cases 1 and 2) where the tumour was resected two days after infusion of the labelled antibody, the resected tumour contained 0.005% of the injected dose of iodine 131 per gram of tumour tissue.

I claim:

1. A method of detecting tumour associated antigens which method comprises:
   (i) preparing samples of hybridoma XMMCO-791 having A.T.C.C. Accession No. HB 9173,
   (ii) separating and purifying the associated antibody XMMCO-791 to obtain the Ig2b isotype,
   (iii) labelling the antibody thus obtained with a radioactive label,
   (iv) preparing a composition containing an effective concentration of said labelled antibody,
   (v) administering said antibody composition to a patient, and
   (vi) screening said patient to detect concentrations of radioactivity thereby indicating a concentration of antibody.

2. A method as claimed in claim 1 wherein the antibody is labelled with $I^{131}$.

3. A method as claimed in claim 2 wherein the screening was effected using a gamma camera.

4. A method as claimed in claim 3 wherein an image enhancement technique is employed.

5. A method as claimed in claim 4 wherein the image enhancement technique includes blood cell and blood transferrin labelling with isotypes selected from at least one of the group consisting of $^{99m}Tc$ and $^{113m}In$.

6. Hybridoma cell line XMMCO-791 having A.T.C.C. Accession No. HB 9173.

7. Monoclonal antibodies or active fragments thereof produced by hybridoma cell line XMMCO-791 having A.T.C.C. Accession No. HB 9173.

* * * * *